US011927667B2

(12) United States Patent
Ferrari

(10) Patent No.: US 11,927,667 B2
(45) Date of Patent: Mar. 12, 2024

(54) SYSTEM AND METHOD FOR DETERMINING SUBSURFACE SOIL LAYER CHARACTERISTICS BASED ON RADAR DATA AND SECONDARY SOIL PARAMETERS

(71) Applicant: CNH Industrial America LLC, New Holland, PA (US)

(72) Inventor: Luca Ferrari, Modena (IT)

(73) Assignee: CNH Industrial America LLC, New Holland, PA (US)

( * ) Notice: Subject to any disclaimer, the term of this patent is extended or adjusted under 35 U.S.C. 154(b) by 516 days.

(21) Appl. No.: 16/523,116

(22) Filed: Jul. 26, 2019

(65) Prior Publication Data
US 2021/0026007 A1    Jan. 28, 2021

(51) Int. Cl.
*G01S 13/88*    (2006.01)
*G01N 33/24*    (2006.01)

(52) U.S. Cl.
CPC .......... *G01S 13/885* (2013.01); *G01N 33/246* (2013.01)

(58) Field of Classification Search
CPC .... G01S 13/885; G01N 33/246; A01B 79/005
USPC .......................................................... 342/22
See application file for complete search history.

(56) References Cited

U.S. PATENT DOCUMENTS

| 4,015,366 | A | * | 4/1977 | Hall, III | ................... | A01G 3/04 |
| | | | | | | 193/25 E |
| 4,200,410 | A | * | 4/1980 | Baker | ..................... | E02F 5/103 |
| | | | | | | 405/181 |
| 5,418,466 | A | | 5/1995 | Watson et al. | | |
| 5,942,899 | A | | 8/1999 | Shrekenhamer et al. | | |

(Continued)

FOREIGN PATENT DOCUMENTS

| RU | 2537908 C2 * | 1/2015 | ............. G01N 33/24 |
| WO | WO-2014153263 A1 * | 9/2014 | ........... E01C 19/235 |

(Continued)

OTHER PUBLICATIONS

I. Woodhead, A. Tan, S. Richards and I. Platt, "Impulse radar—A new sensor for robots," 2015 6th International Conference on Automation, Robotics and Applications (ICARA), 2015, pp. 269-273, doi: 10.1109/ICARA.2015.7081158. (Year: 2015).*

(Continued)

*Primary Examiner* — Nuzhat Pervin
(74) *Attorney, Agent, or Firm* — Rebecca L. Henkel; Rickard K. DeMille

(57) ABSTRACT

In one aspect, a system for determining subsurface soil layer characteristics during the performance of an agricultural operation may include a RADAR sensor configured to capture data indicative of a subsurface soil layer characteristic of the field during the performance of the agricultural operation. Additionally, the system may include a controller communicatively coupled to the RADAR sensor. As such, the controller may be configured to receive the RADAR data (Continued)

from the RADAR sensor and receive an input associated with a secondary soil parameter of the field. Furthermore, the controller may be configured to calibrate the received RADAR data based on the received input. Moreover, the controller may be configured to determine the subsurface soil layer characteristic based on the calibrated RADAR data.

14 Claims, 3 Drawing Sheets

(56) References Cited

U.S. PATENT DOCUMENTS

| | | | |
|---|---|---|---|
| 6,647,799 | B1 | 11/2003 | Raper et al. |
| 6,657,443 | B2 | 12/2003 | Anderson |
| 6,834,550 | B2 | 12/2004 | Upadhyaya et al. |
| 7,068,051 | B2 | 6/2006 | Anderson |
| 7,135,871 | B1* | 11/2006 | Pelletier .................. G01N 22/04 324/640 |
| 7,944,220 | B2 | 5/2011 | Lock |
| 9,222,880 | B2 | 12/2015 | Smith |
| 9,291,710 | B2 | 3/2016 | Debroux et al. |
| 9,348,020 | B2 | 5/2016 | Wilson-Langman et al. |
| 9,723,776 | B2* | 8/2017 | Sporrer ................ A01B 29/048 |
| 9,945,832 | B2 | 4/2018 | Trobat et al. |
| 10,028,425 | B2* | 7/2018 | Canyon ................ A01B 79/005 |
| 10,073,074 | B1* | 9/2018 | Kumar ................. G01N 27/026 |
| 10,542,660 | B2* | 1/2020 | Oliver ..................... F41H 11/14 |
| 10,609,856 | B2* | 4/2020 | Oliver ..................... F41H 11/14 |
| 11,195,109 | B2* | 12/2021 | Mewes .................. G06N 20/00 |
| 2014/0125509 | A1* | 5/2014 | Stolarczyk ........... H01Q 1/3216 342/22 |
| 2014/0365084 | A1* | 12/2014 | Chan ..................... B64D 43/00 701/50 |
| 2016/0029570 | A1* | 2/2016 | Anjum ................. G01N 27/221 700/90 |
| 2016/0109569 | A1* | 4/2016 | Chan ..................... A01C 7/102 239/63 |
| 2017/0176589 | A1* | 6/2017 | Chan .................... A01B 79/005 |
| 2017/0241973 | A1* | 8/2017 | Chan ........................ H04Q 9/00 |
| 2017/0310827 | A1* | 10/2017 | Mehta .................. H04W 80/04 |
| 2017/0336507 | A1* | 11/2017 | Chan ..................... B64D 43/00 |
| 2017/0343485 | A1* | 11/2017 | Garrison .............. G01S 13/003 |
| 2018/0014452 | A1 | 1/2018 | Starr |
| 2018/0054955 | A1* | 3/2018 | Oliver ...................... F42D 3/00 |
| 2018/0184575 | A1* | 7/2018 | Oliver ...................... F41H 7/10 |
| 2018/0306914 | A1* | 10/2018 | Chan ..................... A01C 7/102 |
| 2019/0110392 | A1 | 4/2019 | Gresch et al. |
| 2020/0257997 | A1* | 8/2020 | Mewes .................. A01G 22/00 |
| 2020/0359542 | A1* | 11/2020 | Bögel .................... A01B 33/02 |
| 2021/0190754 | A1* | 6/2021 | Stoller ................... G01N 33/24 |
| 2022/0374912 | A1* | 11/2022 | Zeng ................ G06Q 10/06313 |

FOREIGN PATENT DOCUMENTS

| | | | | |
|---|---|---|---|---|
| WO | WO2017125934 | | 7/2017 | |
| WO | WO2017197292 | | 11/2017 | |
| WO | WO-2019079205 | A1 * | 4/2019 | ............. A01B 47/00 |

OTHER PUBLICATIONS

M. Zribi, "Microwave remote sensing techniques for the analysis of land surface parameters," 2016 International Symposium on Signal, Image, Video and Communications (ISIVC), 2016, pp. 390-395, doi: 10.1109/ISIVC.2016.7894021. (Year: 2016).*

Dong Z, Ye S, Gao Y, Fang G, Zhang X, Xue Z, Zhang T. Rapid Detection Methods for Asphalt Pavement Thicknesses and Defects by a Vehicle-Mounted Ground Penetrating Radar (GPR) System. Sensors (Basel). Dec. 6, 2016;16(12):2067. doi: 10.3390/s16122067. PMID: 27929409; PMCID: PMC5191048. (Year: 2016).*
C. Huang, M. Lu and S. Yi, "The Calibration Processing for Impulse Ground Penetrating Radar," 2006 CIE International Conference on Radar, Shanghai, China, 2006, pp. 1-4, doi: 10.1109/ICR.2006.343414. (Year: 2006).*
Woodhead,A. Tan,S. Richardsandl.Platt,"Impulseradar—Anewsensorforrobots," 20156th International Conferenceon Automation, Roboticsand Applications (ICARA), 2015, pp. 269-273,doi:10.1109/ICARA.2015.7081158.(Year:2015) (Year: 2015).*
M.Zribi, "Microwave remote sensing techniques for the analys isofland surface parameters," 2016 International Symposiumon Signal, Image, Video and Communications (ISIVC), 2016, pp. 390-395,doi:10.1109/ISIVC.2016.7894021.(Year:2016) (Year: 2016).*
Dong Z, Ye S,Gao Y, Fang G, Zhang X, Xue Z, Zhang T. Rapid Detection Methods for Asphalt Pavement Thicknesses and Defects by a Vehicle-Mounted Ground Penetrating Rada r(GPR) System. Sensors(Basel).Dec. 6, 2016;16(12):2067.doi:10.3390/$16122067. PMID:27929409;PMCID:PMC5191048.(Year:2016) (Year: 2016).*
C.Huang, M. LuandS.Yi, "The Calibration Processing for Impulse Ground Penetrating Radar," 2006CIEInternationalConferenceonRadar,Shanghai,China,2006,pp. 1-4,doi:10.1109/ICR.2006.343414. (Year:2006) (Year: 2006).*
Woodhead,A. Tan,S. Richardsandl.Platt,"Impulseradar—Anewsensorforrobots," 20156thInternationalConferenceon Automation,RoboticsandApplications(ICARA),2015,pp. 269-273doi:10.1109/ICARA.2015.7081158.(Year:2015)(Year:2015) (Year:2015).*
Woodhead,A. Tan,S. Richardsandl.Platt,"Impulseradar—Anewsensorforrobots," 20156thInternationalConferenceon Automation, RoboticsandApplications(ICARA),2015,pp. 269-273doi:10.1109/ICARA.2015.7081158.(Year:2015)(Year:2015) (Year:2016).*
Dongz,YeS,GaoY,FangG,ZhangX,XueZ,ZhangT.Rapid DetectionM ethodsforAsphaltPavementThicknessesandDefects byaVehicle-MountedGroundPenetratingRadar(GPR)System.Sensors(Basel). Dec. 6, 2016;16(12):2067.doi:10.3390/$16122067. PMID:27929409;PMCID:PMC5191048.(Year:2016)(Year:2016) (Year: 2016).*
C.Huang,M.LuandS.Yi,"TheCalibrationProcessingforImpulseGrou ndPenetratingRadar," 2006CIEInternationalConference onRadar,Shanghai,China,2006,pp. 1-4,doi:10.1109/ICR.2006.343414. (Year:2006)(Year:2006) (Year: 2006).*
International Search Report and Written Opinion issued in corresponding to Application No. PCT/US2020/042982 dated Nov. 10, 2020 (13 pages).
Husiman, J.A., et al., "Measuring Soil Water Content with Ground Penetrating Radar," Vadose Zone Journal, vol. 2, No. 4, Nov. 2003, pp. 476-491.
Joseph, A. T., et al., "Effects of Corn on C- and L-Band Radar Backscatter: A Correction Method for Soil Moisture Retrieval," Remote Sensing Environment, vol. 114, Issue 11, Nov. 15, 2010, pp. 2417-2430.
Lunt, I.A., et al., "Soil Moisture Content Estimation Using Ground-Penetrating Radar Reflection Data," Journal of Hydrology, vol. 307, Issues 1-4, Jun. 9, 2005, pp. 254-269.
McNairn, Heather, et al., "The Soil Moisture Active Passive Validation Experiment 2012 (SMAPVEX12): Prelaunch Calibration and Validation of the SMAP Soil Moisture Algorithms" IEEE Transactions on Geoscience and Remote Sensing, vol. 53, Issue 5, Nov. 13, 2014, pp. 2784-2801.
Nearing, Grey S., et al., "Likelihood Parameter Estimation for Calibrating a Soil Moisture Model Using Radar Backscatter," Remote Sensing of Environment, vol. 114, Issue 11, Nov. 15, 2010, pp. 2564-2574.

* cited by examiner

SYSTEM AND METHOD FOR DETERMINING SUBSURFACE SOIL LAYER CHARACTERISTICS BASED ON RADAR DATA AND SECONDARY SOIL PARAMETERS

FIELD OF THE INVENTION

The present disclosure generally relates to agricultural machines and, more particularly, to systems and methods for determining subsurface soil layer characteristics of a field based on RADAR data and one or secondary soil parameters of the field.

BACKGROUND OF THE INVENTION

It is well known that, to attain the best agricultural performance from a piece of land, a farmer must cultivate the soil, typically through a tillage operation. Common tillage operations include plowing, harrowing, and subsoiling. Modern farmers perform these tillage operations by pulling a tillage implement behind an agricultural work vehicle, such as a tractor. Depending on the crop selection and the soil conditions, a farmer may need to perform several tillage operations at different times over a crop cycle to properly cultivate the land to suit the crop choice.

When performing a tillage operation, it is desirable to create a level and uniform layer of tilled soil across the field to form a proper seedbed for subsequent planting operations. Furthermore, it is generally desirable to break up any layers of subsurface soil that have been compacted (e.g., due to vehicle traffic, ponding, and/or the like). In this regard, tillage implements often include one or more sensors mounted thereon to monitor various subsurface soil layer characteristics during the performance of such tillage operations. For example, some tillage implements include one or more radio detection and ranging (RADAR) sensors that capture radar data of the subsurface soil layer(s) within the field. However, varying soil conditions across the field and/or other factors may cause the captured radar data to provide an inaccurate indication(s) of the subsurface soil layer characteristic(s).

Accordingly, an improved system and method for determining subsurface soil layer characteristics would be welcomed in the technology.

SUMMARY OF THE INVENTION

Aspects and advantages of the technology will be set forth in part in the following description, or may be obvious from the description, or may be learned through practice of the technology.

In one aspect, the present subject matter is directed to a system for determining subsurface soil layer characteristics during the performance of an agricultural operation. The system may include an agricultural machine configured to perform an agricultural operation on a field across which the agricultural machine is traveling. The system may also include a RADAR sensor provided in operative association with the agricultural machine, with the RADAR sensor configured to capture data indicative of a subsurface soil layer characteristic of the field. Additionally, the system may include a controller communicatively coupled to the RADAR sensor. As such, the controller may be configured to receive the RADAR data from the RADAR sensor and receive an input associated with a secondary soil parameter of the field. Furthermore, the controller may be configured to calibrate the received RADAR data based on the secondary soil parameter. Moreover, the controller may be configured to determine the subsurface soil layer characteristic based on the calibrated RADAR data.

In another aspect, the present subject matter is directed to a method for determining subsurface soil layer characteristics during the performance of an agricultural operation. The method may include receiving, with one or more computing devices, RADAR data indicative of a subsurface soil layer characteristic of a field on which the agricultural operation is being performed. Additionally, the method may include receiving, with the one or more computing devices, an input associated with a secondary soil parameter of the field. Furthermore, the method may include calibrating, with the one or more computing devices, the received RADAR data based on the secondary soil characteristic. Moreover, the method may include determining, with the one or more computing devices, the subsurface soil layer characteristic based on the calibrated RADAR data.

These and other features, aspects and advantages of the present technology will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present technology, including the best mode thereof, directed to one of ordinary skill in the art, is set forth in the specification, which makes reference to the appended figures, in which.

Figure 1:
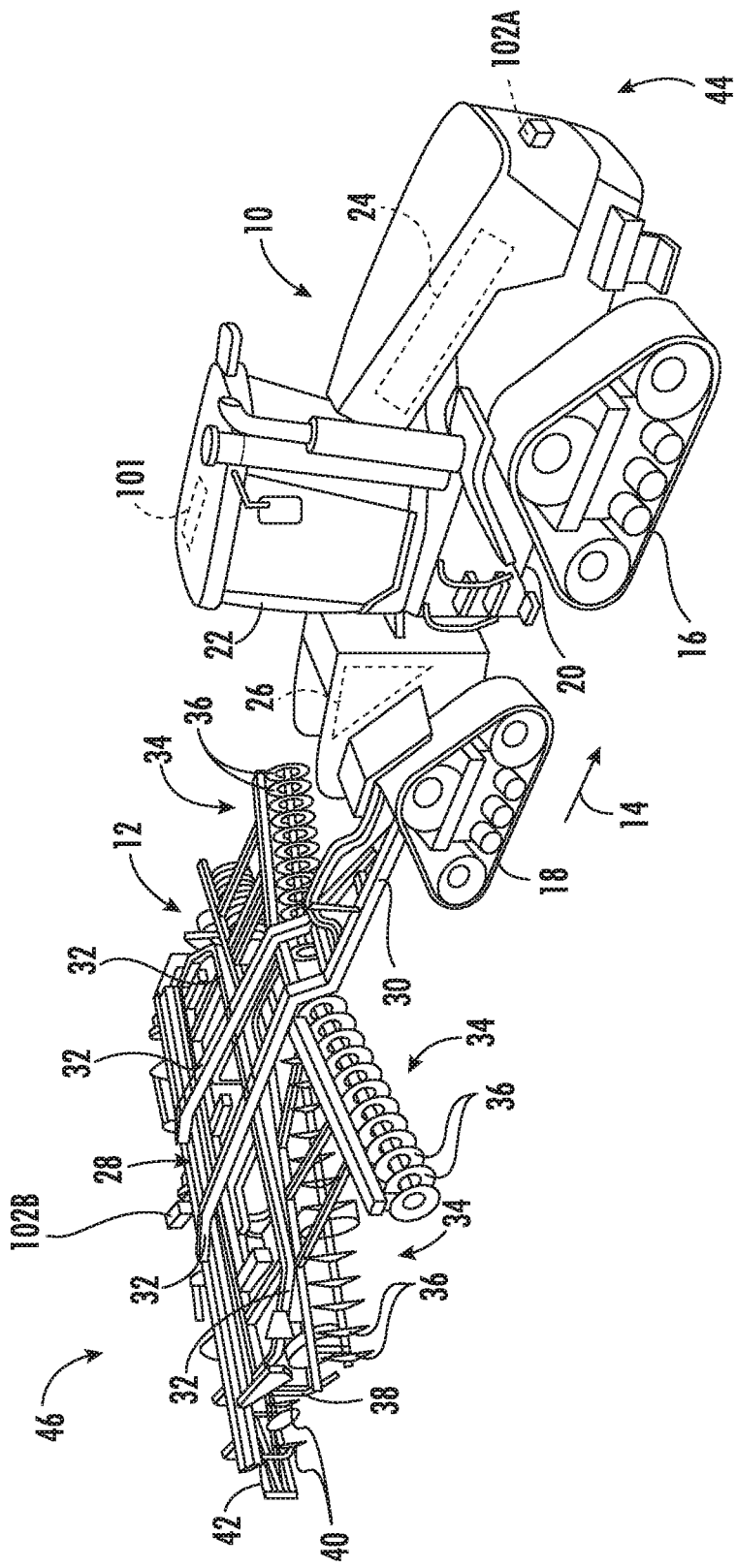
FIG. 1 illustrates a perspective view of one embodiment of an agricultural machine in accordance with aspects of the present subject matter.

Repeat use of reference characters in the present specification and drawings is intended to represent the same or analogous features or elements of the present technology.

DETAILED DESCRIPTION OF THE DRAWINGS

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems and methods for determining subsurface soil layer characteristics during the performance of an agricultural operation. Specifically, in several embodiments, a controller of the disclosed system may be configured to receive radio detection and ranging (RADAR) data from one or more RADAR sensors coupled to or mounted on an agricultural machine during the performance of the agricultural operation. Such RADAR data may, in turn, be indicative of one or more subsurface soil layer characteristics (e.g., the presence and/or location of a compaction layer, the depth of a seedbed, and/or the like) of the field. Furthermore, the controller may be configured to receive an input(s) associated with one or more secondary soil parameters (e.g., soil moisture, salinity, oxygen content/porosity, and/or the like) of the field. For example, in one embodiment, the controller may be configured to receive an input associated with the soil moisture content of the field from a soil moisture sensor coupled to the agricultural machine during the performance of the agricultural operation. Moreover, the controller may be configured to received inputs associated with the soil salinity and/or soil oxygen content/porosity from an operator of the agricultural machine (e.g., via a user interface of the machine).

In accordance with aspects of the present subject matter, the controller may be configured to calibrate the received RADAR data based on the secondary soil parameter(s). Specifically, in several embodiments, the controller may be configured to determine one or more correction factors for the RADAR data based on the secondary soil parameter(s). For example, in one embodiment, the controller may be configured to access one or more look-up tables stored within its memory device(s), with each table correlating the one or more of secondary soil parameters with an associated correction factor. Moreover, the controller may be configured to adjust or modify the received RADAR data (e.g., the time-of-flight, amplitude, frequency, and/or phase of an echo signal(s) associated with such RADAR data) based on the determined correction factor(s) to calibrate the RADAR data. Thereafter, the controller may be configured to determine the subsurface soil layer characteristic(s) based on the calibrated RADAR data.

Referring now to the drawings, FIG. 1 illustrates a perspective view of one embodiment of an agricultural machine in accordance with aspects of the present subject matter. As shown, in the illustrated embodiment, the agricultural machine corresponds to a work vehicle 10 and an associated agricultural implement 12. In general, the work vehicle 10 may be configured to tow the implement 12 across a field in a direction of travel (e.g., as indicated by arrow 14 in FIG. 1). As such, in one embodiment, the work vehicle 10 may be configured as an agricultural tractor and the implement 12 may be configured as a tillage implement. However, in other embodiments, the work vehicle 10 may be configured as any other suitable type of vehicle, such as an agricultural harvester, a self-propelled sprayer, and/or the like. Similarly, the implement 12 may be configured as any other suitable type of implement, such as a planter. Furthermore, it should be appreciated that the agricultural machine may correspond to any suitable powered and/or unpowered agricultural machine (including suitable vehicles and/or equipment, such as only a work vehicle or only an implement). Additionally, the agricultural machine may include more than two machines (e.g., a tractor, a planter, and an associated air cart) coupled to a work vehicle.

As shown in FIG. 1, the work vehicle 10 may include a pair of front track assemblies 16, a pair or rear track assemblies 18, and a frame or chassis 20 coupled to and supported by the track assemblies 16, 18. An operator's cab 22 may be supported by a portion of the chassis 20 and may house various input devices (e.g., a user interface) for permitting an operator to control the operation of one or more components of the work vehicle 10 and/or one or more components of the implement 12. Additionally, the work vehicle 10 may include an engine 24 and a transmission 26 mounted on the chassis 20. The transmission 26 may be operably coupled to the engine 24 and may provide variably adjusted gear ratios for transferring engine power to the track assemblies 16, 18 via a drive axle assembly (not shown) (or via axles if multiple drive axles are employed).

Additionally, as shown in FIG. 1, the implement 12 may generally include a frame 28 configured to be towed by the vehicle 10 via a pull hitch or tow bar 30 in the direction of travel 14. In general, the frame 28 may include a plurality of structural frame members 32, such as beams, bars, and/or the like, configured to support or couple to a plurality of components. As such, the frame 28 may be configured to support a plurality of ground-engaging tools, such as a plurality of shanks, disk blades, leveling blades, basket assemblies, tines, spikes, and/or the like. In one embodiment, the various ground-engaging tools may be configured to perform a tillage operation or any other suitable ground-engaging operation on the field across which the implement 12 is being towed. For example, in the illustrated embodiment, the frame 28 is configured to support various gangs 34 of disc blades 36, a plurality of ground-engaging shanks 38, a plurality of leveling blades 40, and a plurality of crumbler wheels or basket assemblies 42. However, in alternative embodiments, the frame 28 may be configured to support any other suitable ground-engaging tool(s) or combinations of ground-engaging tools.

Moreover, a location sensor 101 may be provided in operative association with the vehicle 10 and/or the implement 12. For instance, as shown in FIG. 1, the location sensor 101 is installed on or within the vehicle 10. However, in other embodiments, the location sensor 101 may be installed on or within the implement 12. In general, the location sensor 101 may be configured to determine the current location of the vehicle 10 and/or the implement 12 using a satellite navigation positioning system (e.g. a GPS system, a Galileo positioning system, the Global Navigation satellite system (GLONASS), the BeiDou Satellite Navigation and Positioning system, and/or the like). In such an embodiment, the location determined by the location sensor 101 may be transmitted to a controller(s) of the vehicle 10 and/or the implement 12 (e.g., in the form coordinates) and stored within the controller's memory for subsequent processing and/or analysis. For instance, based on the known dimensional configuration and/or relative positioning between the vehicle 10 and the implement 12, the determined location from the location sensor 101 may be used to geo-locate the implement 12 within the field.

In accordance with aspects of the present subject matter, the vehicle/implement 10/12 may include one or more radio detection and ranging (RADAR) sensors coupled thereto and/or mounted thereon. As will be described below, each RADAR sensor may be configured to capture RADAR data associated with a portion of the field across which the vehicle/implement 10/12 is traveling. The captured RADAR data may, in turn, be indicative of one or more subsurface soil layer characteristics of the field. For example, such characteristics may include the presence and/or location of a subsurface soil compaction layer, the depth of a seedbed, and/or the like. As such, in several embodiments, the RADAR sensor(s) may be provided in operative association with the vehicle/implement 10/12 such that the sensor(s) has an associated field(s) of view or sensor detection range(s) directed towards a portion(s) of the field adjacent to the vehicle/implement 10/12. For example, as shown in FIG. 1, in one embodiment, one RADAR sensor 102A may be mounted on a forward end 44 of the work vehicle 10 to capture RADAR data associated with a section of the field disposed in front of the vehicle 10 relative to the direction of travel 14. Similarly, as shown in FIG. 1, a second RADAR sensor 102B may be mounted on an aft end 46 of the implement 12 to capture RADAR data associated with a section of the field disposed behind the implement 12 relative to the direction of travel 14. However, in alternative embodiments, the RADAR sensors 102A, 102B may be installed at any other suitable location(s) on the vehicle/implement 10/12. Additionally, in some embodiments, the vehicle/implement 10/12 may include only one RADAR sensor or three or more RADAR sensors.

It should be further appreciated that the configuration of the work vehicle 10 and the agricultural implement 12 described above and shown in FIG. 1 is provided only to place the present subject matter in an exemplary field of use. Thus, it should be appreciated that the present subject matter may be readily adaptable to any manner of agricultural machine configuration.

Figure 2:
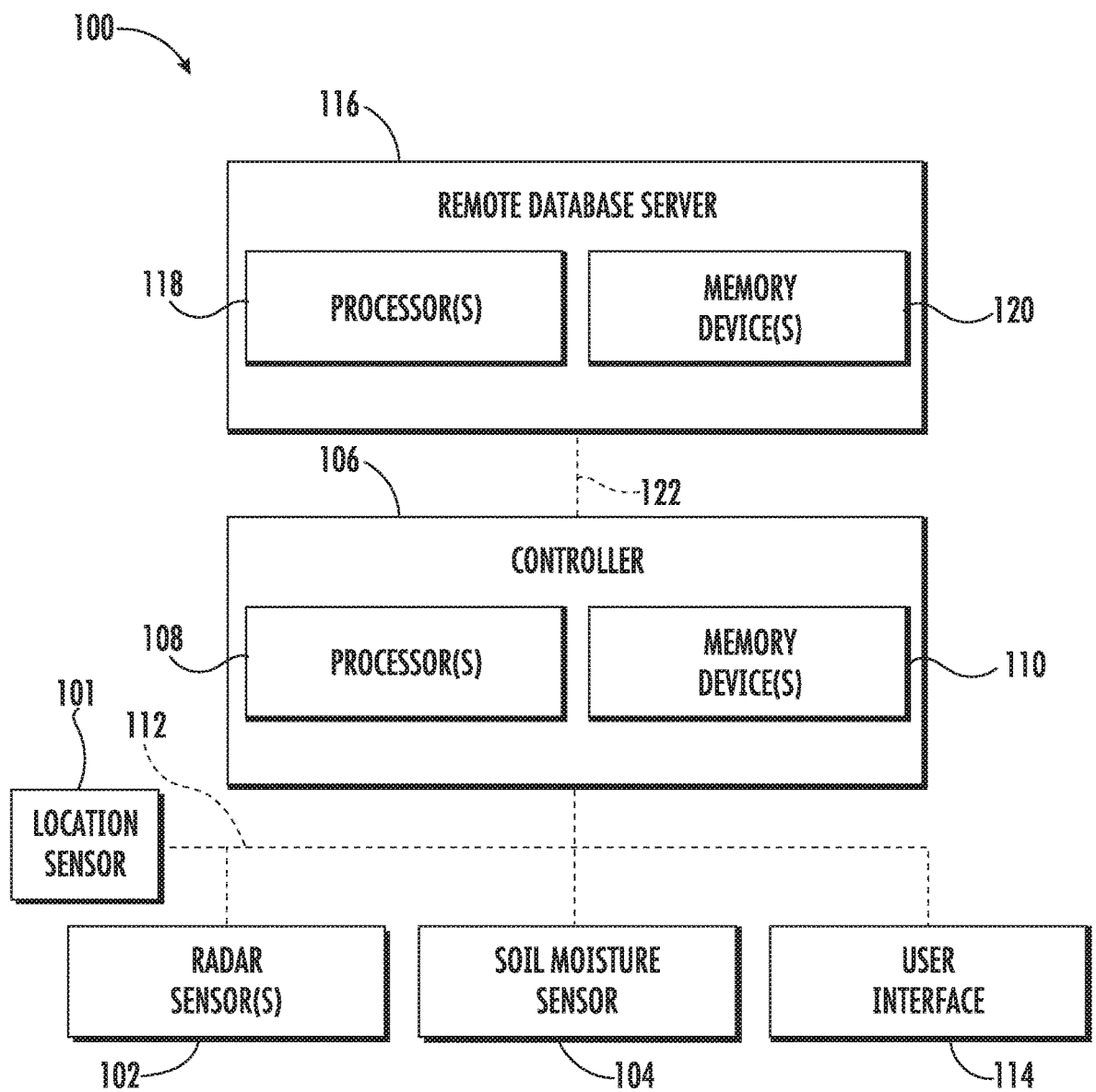
FIG. 2 illustrates a schematic view of one embodiment of a system for determining subsurface soil layer characteristics during the performance of an agricultural operation in accordance with aspects of the present subject matter.

Referring now to FIG. 2, a schematic view of one embodiment of a system 100 for determining subsurface soil layer characteristics during the performance of an agricultural operation is illustrated in accordance with aspects of the present subject matter. In general, the system 100 will be described herein with reference to the work vehicle 10 and the agricultural implement 12 described above with reference to FIG. 1. However, it should be appreciated by those of ordinary skill in the art that the disclosed system 100 may generally be utilized with agricultural machines having any other suitable machine configuration As shown in FIG. 2, the system 100 may include one or more RADAR sensor(s) 102 coupled to or otherwise mounted on the vehicle/implement 10/12. Specifically, in several embodiments, as the vehicle/implement 10/12 travel across the field, the RADAR sensor(s) 102 may be configured to emit one or more radio wave and/or microwave output signals directed toward a portion of the field surface within the corresponding field of view or sensor detection zone. The output signal(s) may, in turn, be reflected by one or more subsurface soil layers (e.g., the compaction layer) as echo signal(s). Moreover, the RADAR sensor(s) 102 may be configured to receive the reflected echo signal(s). In this regard, the time of flight, amplitude, frequency, and/or phase of the received echo signal(s) may be indicative of subsurface soil layer characteristic(s) of the field. As such, the RADAR sensor(s) 102 may correspond to any suitable type of RADAR-based sensing device(s), such as a ground-penetrating RADAR (GPR) sensor(s), a multiple-input-multiple-output (MIMO) radar sensor(s), a polarimetric radar sensor(s), and/or the like.

Additionally, the system 100 may include a soil moisture sensor 104 coupled to or otherwise mounted on the vehicle/implement 10/12. In general, the soil moisture sensor 104 may be configured to capture data indicative of the soil moisture content of the field across which the vehicle/implement 10/12 is traveling. For example, in one embodiment, the soil moisture sensor 104 may be configured as an optical sensor configured to detect one or more characteristics of light reflected by the soil, with such characteristics generally being indicative of the soil moisture content. However, in alternative embodiments, the soil moisture sensor 104 may be configured as any other suitable device for sensing or detecting the soil moisture content of the field.

In accordance with aspects of the present subject matter, the system 100 may include a controller 106 positioned on and/or within or otherwise associated with the vehicle 10 and/or the implement 12. In general, the controller 106 may comprise any suitable processor-based device known in the art, such as a computing device or any suitable combination of computing devices. Thus, in several embodiments, the controller 106 may include one or more processor(s) 108 and associated memory device(s) 110 configured to perform a variety of computer-implemented functions. As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 110 of the controller 106 may generally comprise memory element(s) including, but not limited to, a computer readable medium (e.g., random access memory (RAM)), a computer readable non-volatile medium (e.g., a flash memory), a floppy disc, a compact disc-read only memory (CD-ROM), a magneto-optical disc (MOD), a digital versatile disc (DVD), and/or other suitable memory elements. Such memory device(s) 110 may generally be configured to store suitable computer-readable instructions that, when implemented by the processor(s) 108, configure the controller 106 to perform various computer-implemented functions.

In addition, the controller 106 may also include various other suitable components, such as a communications circuit or module, a network interface, one or more input/output channels, a data/control bus and/or the like, to allow controller 106 to be communicatively coupled to any of the various other system components described herein (e.g., the location sensor 101, the RADAR sensor(s) 102, and/or the soil moisture sensor 104). For instance, as shown in FIG. 2, a communicative link or interface 112 (e.g., a data bus) may be provided between the controller 106 and the sensors 101, 102, 104 to allow the controller 106 to communicate with the sensors 101, 102, 104 via any suitable communications protocol (e.g., CANBUS).

It should be appreciated that the controller 106 may correspond to an existing controller(s) of the vehicle 10 and/or the implement 12, itself, or the controller 106 may correspond to a separate processing device. For instance, in one embodiment, the controller 106 may form all or part of a separate plug-in module that may be installed in association with the vehicle 10 and/or the implement 12 to allow for the disclosed systems to be implemented without requiring additional software to be uploaded onto existing control devices of the vehicle 10 and/or the implement 12. It should also be appreciated that the functions of the controller 106 may be performed by a single processor-based device or may be distributed across any number of processor-based devices, in which instance such devices may be considered to form part of the controller 106. For instance, the functions of the controller 106 may be distributed across multiple application-specific controllers, such as an engine controller, a transmission controller, an implement controller, and/or the like.

Furthermore, in one embodiment, the system 100 may also include a user interface 114. More specifically, the user interface 114 may be configured to receive inputs (e.g., inputs associated with the soil salinity and/or oxygen content/porosity of the field) from the operator of the vehicle/implement 10/12. As such, the user interface 114 may include one or more input devices (not shown), such as touchscreens, keypads, touchpads, knobs, buttons, sliders, switches, mice, microphones, and/or the like, which are configured to receive the operator inputs. Furthermore, the user interface 114 may be communicatively coupled to the controller 106 via the communicative link 112 to permit the received operator inputs to be transmitted from the user interface 114 to the controller 106. In addition, some embodiments of the user interface 114 may include one or more feedback devices (not shown), such as display screens, speakers, warning lights, and/or the like, which are configured to provide feedback from the controller 106 to the operator. In one embodiment, the user interface 114 may be mounted or otherwise positioned within the cab 22 of the vehicle 10. However, in alternative embodiments, the user interface 114 may mounted at any other suitable location.

Moreover, the system 100 may include a remote database server 116 configured to store data associated with one or more previously captured or determined secondary soil parameter(s) (e.g., the soil moisture content, salinity, and/or oxygen content/porosity) of the field across which the vehicle/implement 10/12 is traveling. In general, the remote database server 116 may comprise any suitable processor-based device known in the art, such as a computing device or any suitable combination of computing devices. Thus, in several embodiments, the remote database server 116 may include one or more processor(s) 118 and associated memory device(s) 120 configured to perform a variety of computer-implemented database server functions. Such memory device(s) 120 may generally be configured to store suitable computer-readable instructions that, when implemented by the processor(s) 118, configure the remote database server 116 to perform various computer-implemented database server functions.

Furthermore, the remote database server 116 may also include various other suitable components, such as a communications circuit or module, a network interface, one or more input/output channels, a data/control bus and/or the like, to allow remote database server 116 to be communicatively coupled to the controller 106. For instance, as shown in FIG. 2, a communicative link or interface 122 (e.g., a data bus) may be provided between the remote database server 116 and the controller 106 to allow the remote database server 116 and the controller 106 to communicate via any suitable communications protocol (e.g., Wi-Fi, 3G, 4G, LTE, and/or the like).

Additionally, it should be appreciated that the remote database server 116 may located at any suitable location that is remote or otherwise spaced apart from the vehicle 10 and the implement 12. For example, in one embodiment, the remote database server 116 may be located at a farm management office or facility. However, in alternative embodiments, the remote database server 116 may be located at any other suitable location.

In several embodiments, the controller 106 may be configured to receive RADAR data from one or more RADAR sensors 102. As described above, the vehicle/implement 10/12 may include one or more RADAR sensors 102, with each RADAR sensor 102 configured to capture RADAR data of a portion of the field within its field of view. In this regard, as the vehicle/implement 10/12 travels across the field to perform an agricultural operation (e.g., a tillage operation) thereon, the controller 106 may be configured to receive RADAR data from the RADAR sensor(s) 102 (e.g., via the communicative link 112). As will be described below, the controller 106 may be configured to calibrate the received RADAR data and use the calibrated RADAR data to determine one or more subsurface soil characteristics (e.g., the presence and/or location of a compaction layer and/or the seedbed depth) of the field across which the vehicle/implement 10/12 is traveling.

Furthermore, the controller 106 may be configured to receive one or more inputs associated with a secondary soil parameter(s) of the field. Such secondary soil parameter(s) may include the soil moisture content of the field, the soil salinity of the field, soil oxygen content or porosity of the field, and/or the like. As will be described below, the controller 106 may be configured to calibrate the received RADAR data based on the secondary soil parameter(s) such that the calibrated RADAR data provides an accurate indication of the subsurface soil layer characteristic(s).

In several embodiments, the controller 106 may be configured to receive the input(s) associated with a secondary soil parameter(s) from a sensor(s) provided in operative association with the vehicle/implement 10/12. In general, certain secondary soil parameters, such as soil moisture content, may vary greatly across the field. As such, in one embodiment, the controller 106 may be configured to receive an input(s) associated with the soil moisture content of the field from a soil moisture sensor 104. More specifically, as described above, the vehicle/implement 10/12 may include a soil moisture sensor 104 configured to capture data indicative of the soil moisture content of the field. In this regard, as the vehicle/implement 10/12 travels across the field, the controller 106 may receive the sensor data from the soil moisture sensor 104 (e.g., via the communicative link 112). Thereafter, the controller 106 may be configured to process/analyze the received sensor data to determine or estimate a soil moisture content value of the field at the current location of the vehicle/implement 10/12. For instance, the controller 106 may include a look-up table(s), suitable mathematical formula, and/or algorithms stored within its memory device(s) 110 that correlates the received sensor data to the soil moisture content of the field. Additionally, the controller 106 may be configured to update the determined soil moisture content value at a predetermined rate (e.g., the sampling rate of the soil moisture sensor 104) based on newly received sensor data as the vehicle/implement 10/12 is moved across the field. In this regard, each determined soil moisture content value may change as the soil moisture content of the field varies. However, in alternative embodiments, the controller 106 may be configured to receive an input(s) indicative of any other secondary soil parameter(s), such as the soil salinity and/or soil oxygen content/porosity of the field, from one or more sensors provided in operative association with the vehicle/implement 10/12.

Moreover, in several embodiments, the controller 106 may be configured to receive the input(s) associated with a secondary soil parameter(s) from an operator of the vehicle/implement 10/12. In general, certain secondary soil parameters, such as soil salinity and oxygen content/porosity, may vary little across the field such that a single value for such parameter(s) may be indicative of the entire field. As such, in one embodiment, the controller 106 may be configured to receive an input(s) associated with the soil salinity and/or the soil oxygen content/porosity of the field from the operator of the vehicle/implement 10/12. More specifically, as described above, the vehicle/implement 10/12 may include a user interface 114 configured to receive operator inputs associated with the soil salinity and/or oxygen content of the field from the operator. As such, the vehicle/implement operator may determine (e.g., by testing one or more soil samples from the field) the soil salinity and/or oxygen content/porosity for the field on which the agricultural operation is to be performed. The operator may then interact with the input device(s) of the user interface 114 to provide the determined soil salinity and/or oxygen content/porosity values to the user interface 114. Thereafter, the soil salinity and/or oxygen content/porosity values may be transmitted from the user interface 114 to the controller 106 (e.g., via the communicative link 112). However, in alternative embodiments, the controller 106 may be configured to receive an input(s) indicative of any other secondary soil parameter(s), such as the soil moisture content of the field, from the operator of the vehicle/implement 10/12.

Furthermore, in several embodiments, the secondary soil parameter(s) may be geo-referenced to the current location of the vehicle/implement 10/12 within the field. In such embodiments, the secondary soil parameter data stored in the remote database server 118 and/or the memory 110 of the controller 106 may be geo-referenced to specific locations within the field. In this regard, as the vehicle/implement 10/12 travels across the field, the controller 106 may be configured to geo-locate the vehicle/implement 10/12 within the field based on the data (e.g., coordinates) received from the location sensor 101 (e.g., via the communicative link 112). As such, the controller 106 may be configured to determine the current location the implement/vehicle 10/12 within the field based on the geo-located position of the implement/vehicle 10/12. Thereafter, the controller 106 may be configured to access the secondary soil characteristic data associated with such location of the field from its memory 110 and/or request such secondary soil parameter data from the remote database server 116.

It should be appreciated that, in several embodiments, the controller 106 may be configured to receive the input(s) associated with the secondary soil parameter(s) from a combination of its memory 110, sensors, the operator of the vehicle/implement 10/12, and remote database servers/remote devices. For example, in one embodiment, the controller 106 may be configured to receive an input associated with the soil moisture content of the field from the soil moisture sensor 104 coupled to the vehicle/implement 10/12 and inputs associated with the soil salinity and the soil oxygen content/porosity from the operator (e.g., via the user interface 114).

Additionally, it should be appreciated that the controller 106 may be configured to receive an input(s) associated with any suitable number of secondary soil parameters. For example, as indicated above, in one embodiment, the controller 106 may be configured to receive inputs associated with three secondary soil parameters (e.g., the soil moisture content, salinity, and oxygen content/porosity) of the field. However, in alternative embodiments, the controller 106 may be configured to receive inputs associated with a single secondary soil parameter (e.g., one of the soil moisture content, salinity, or oxygen content/porosity), two secondary soil parameters (e.g., two of the soil moisture content, salinity, or oxygen content/porosity) or more than three secondary soil parameters (e.g., the soil moisture content, salinity, and oxygen content/porosity in addition to other parameter(s)).

In general, variations in the soil conditions across the field may impact the accuracy of the subsurface soil layer characteristic determinations based on the received RADAR data. More specifically, moisture and salt may increase the amount that the soil absorbs or attenuates the output signal(s) emitted by the RADAR sensor(s) 102. However, oxygen content/porosity may decrease the amount that the soil absorbs or attenuates the output signal(s) emitted by the RADAR sensor(s) 102. As such, RADAR data captured in portion of the field having high soil moisture content, high soil salinity, and/or low soil oxygen content/porosity may indicate that the compaction layer is shallower than it really is. Furthermore, such RADAR data may result in a determination that the seedbed floor is shallower than it really is. Conversely, RADAR data captured in portion of the field having low soil moisture content, low soil salinity, and/or high soil oxygen content/porosity may result in a determination that the compaction layer is deeper than it really is. Furthermore, such RADAR data may result in a determination that the seedbed floor is deeper than it really is.

In accordance with aspects of the present subject matter, the controller 106 may be configured to calibrate the received RADAR data based on the secondary soil parameter(s). In general, the controller 106 may be configured to adjust or otherwise modify the received RADAR based on the secondary soil parameter(s) such that the calibrated RADAR data provides an accurate indication of the subsurface soil layer characteristic(s) of the soil. Specifically, in several embodiments, the controller 106 may be configured to determine one or more correction factor(s) for the RADAR data based on the secondary soil parameter(s). Thereafter, the controller 106 may be configured to adjust the one or more parameters of the received RADAR data based on the determined correction factor(s) to calibrate the RADAR data. Such parameters may include the time of flight, amplitude, frequency, and/or phase of the received echo signal(s) associated with the received RADAR data. For example, in one embodiment, the determined correction factor(s) may correspond to a single numerical value(s) that is mathematically combined with (e.g., multiplied by) the value(s) associated with the parameter(s) of the received RADAR data. Additionally, in some embodiments, a correction factor may be determined for each parameter associated with the received RADAR data that is used in determining the subsurface soil layer characteristic(s).

It should be appreciated that the controller 106 may be configured to determine the correction factor(s) for the received RADAR data in any suitable manner. As indicated above, in several embodiments, each correction factor may correspond to a single numerical value. For example, in such embodiments, the controller 106 may be configured to access one or more look-up tables stored within its memory device(s) 110. Each look-up table may, in turn, provide a correction factor value associated with a corresponding secondary soil parameter value or combination of secondary soil parameter values. In another embodiment, the controller 106 may be configured to calculate the correction factor(s) from the secondary soil parameter(s) using one or more mathematical formula stored within its memory device(s) 110. However, in alternative embodiments, the controller 106 may be configured to calibrate the received RADAR data in a more complex manner. For instance, the controller 106 may calibrate the received RADAR data using one or more suitable algorithms that modify the RADAR data in a more complex manner, such as by modifying the shape(s) of the echo signal(s) associated with the such data, based on the secondary soil parameter(s).

Furthermore, the controller 106 may be configured to determine one or more subsurface soil layer characteristics based on the calibrated RADAR data. Such subsurface soil layer characteristics may include the presence of a subsurface soil compaction layer, the location/depth of the compaction layer, the depth of a seedbed floor, and/or the like. In general, as described above, the calibrated RADAR data may provide an accurate indication of the subsurface soil layer characteristic(s) of the field by taking into account the soil conditions of the field. As such, the controller 106 may be configured to process/analyze the calibrated RADAR data to determine or estimate the subsurface soil layer characteristic(s) of the field at the current location of the vehicle/implement 10/12. For instance, the controller 106 may include a look-up table(s), suitable mathematical formula, and/or algorithms stored within its memory device(s) 110 that correlates the calibrated RADAR data to the subsurface soil layer characteristic(s) of the field.

Figure 3:
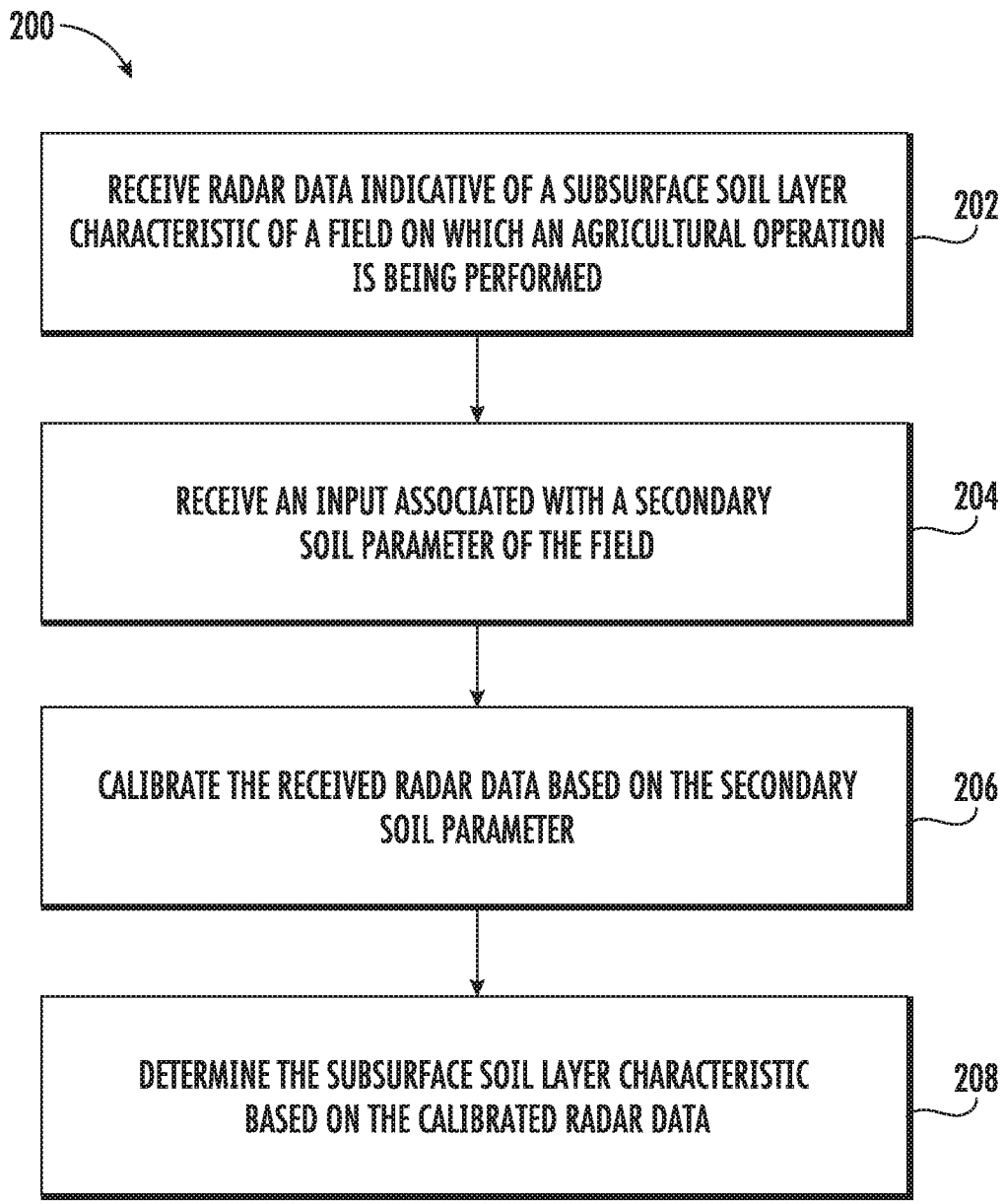
FIG. 3 illustrates a flow diagram of one embodiment of a method for determining subsurface soil layer characteristics during the performance of an agricultural operation in accordance with aspects of the present subject matter.

Referring now to FIG. 3, a flow diagram of one embodiment of a method 200 for determining subsurface soil layer characteristics during the performance of an agricultural operation is illustrated in accordance with aspects of the present subject matter. In general, the method 200 will be described herein with reference to the work vehicle 10, the agricultural implement 12, and the system 100 described above with reference to FIGS. 1 and 2. However, it should be appreciated by those of ordinary skill in the art that the disclosed method 200 may generally be implemented with any agricultural machines having any suitable machine configuration and/or any system having any suitable system configuration. In addition, although FIG. 3 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 3, at (202), the method 200 may include receiving, with one or more computing devices, RADAR data indicative of a subsurface soil layer characteristic of a field on which an agricultural operation is being performed. For instance, as described above, as a work vehicle 10 or an agricultural implement 12 performs an agricultural operation on a field, the controller 106 may be configured to receive RADAR data from one or more RADAR sensors 102 coupled to or mounted on the vehicle/implement 10/12. The RADAR data may, in turn, be indicative of one or more subsurface soil layer characteristics of field, such as the presence of a compaction layer, the location/depth of the compaction, depth of the seedbed, and/or the like.

Additionally, at (204), the method 200 may include receiving, with the one or more computing devices, an input associated with a secondary soil parameter of the field. For instance, as described above, the controller 106 may be configured to receive one or more inputs from an operator (e.g., via the user interface 114) and/or a sensor (e.g., the soil moistures sensor 104) of the vehicle/implement 10/12. Such input(s) may, in turn, be indicative of one or more secondary soil parameters, such as the soil moisture content, salinity and/or oxygen content/porosity of the field.

Moreover, as shown in FIG. 3, at (206), the method 200 may include calibrating, with the one or more computing devices, the received RADAR data based on the secondary soil parameter. For instance, as described above, the controller 106 may be configured to calibrate the received RADAR data based on the received secondary soil characteristic(s).

Furthermore, at (208), the method 200 may include determining, with the one or more computing devices, the subsurface soil layer characteristic based on the calibrated RADAR data. For instance, as described above, the controller 106 may be configured to determine the subsurface soil layer characteristic(s) based on the calibrated RADAR data.

It is to be understood that the steps of the method 200 are performed by the controller 106 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, any of the functionality performed by the controller 106 described herein, such as the method 200, is implemented in software code or instructions which are tangibly stored on a tangible computer readable medium. The controller 106 loads the software code or instructions via a direct interface with the computer readable medium or via a wired and/or wireless network. Upon loading and executing such software code or instructions by the controller 106, the controller 106 may perform any of the functionality of the controller 106 described herein, including any steps of the method 200 described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

This written description uses examples to disclose the technology, including the best mode, and also to enable any person skilled in the art to practice the technology, including making and using any devices or systems and performing any incorporated methods. The patentable scope of the technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

The invention claimed is:

1. A system for determining subsurface soil layer characteristics during the performance of an agricultural operation, the system comprising:
   an agricultural machine configured to perform an agricultural operation on a field across which the agricultural machine is traveling;
   a RADAR sensor provided in operative association with the agricultural machine, the RADAR sensor configured to capture RADAR data indicative of at least one of a presence of a compaction layer within the field, a location of the compaction layer within the field, or a seedbed depth within the field; and
   a controller communicatively coupled to the RADAR sensor, wherein the controller:
   receives the RADAR data from the RADAR sensor;
   receives first input associated with a soil moisture content of the field;
   determines a soil moisture content value for the field based on the received first input;
   receives a second input associated with a soil oxygen content of the field;
   determines a soil oxygen content value for the field based on the received second input;

determines a correction factor for the RADAR data based on the determined soil moisture content value and the determined soil oxygen content value;

adjusts the received RADAR data based on the determined correction factor to calibrate the RADAR data; and determines the at least one of the presence of the compaction layer within the field, the location of the compaction layer within the field, or the seedbed depth within the field based on the calibrated RADAR data.

2. The system of claim 1, wherein the controller adjusts at least one of a time-of-flight, an amplitude, a frequency, and/or a phase associated with the received RADAR data based on the determined correction factor.

3. The system of claim 1, further comprising:

a soil moisture sensor configured to capture data indicative of the soil moisture content of the field as the agricultural machine travels across the field, the soil moisture sensor communicatively coupled to the controller, wherein, when receiving the first input, the controller receives the first input associated with the soil moisture content of the field from the soil moisture sensor.

4. The system of claim 3, wherein the controller updates the determined soil moisture content value at a predetermined rate as the agricultural machine is moved across the field.

5. The system of claim 1, wherein, when receiving the first input, the controller receives the first input associated with the soil moisture content of the field from at least one of an operator of the agricultural machine or a remote server database.

6. The system of claim 1, wherein the at least one of the presence of the compaction layer within the field, the location of the compaction layer within the field, or the seedbed depth within the field corresponds to the at least one of the presence of the compaction layer within the field or the location of the compaction layer within the field.

7. The system of claim 1, wherein the at least one of the presence of the compaction layer within the field, the location of the compaction layer within the field, or the seedbed depth within the field corresponds to the seedbed depth within the field.

8. A method for determining subsurface soil layer characteristics during the performance of an agricultural operation, the method comprising:

receiving, with one or more computing devices, RADAR data indicative of at least one of a presence of a compaction layer within the field, a location of the compaction layer within the field, or a seedbed depth within the field on which the agricultural operation is being performed;

receiving, with the one or more computing devices, first input associated with a soil moisture content of the field;

determining, with the one or more computing devices, a soil moisture content value of the field based on the received first input;

receiving, with the one or more computing devices, a second input associated with a soil oxygen content of the field;

determining, with the one or more computing devices, a soil oxygen content value of the field based on the received second input;

determining, with the one or more computing devices, a correction factor for the RADAR data based on the determined soil moisture content value and the determined soil oxygen content value;

adjusting, with the one or more computing devices, the received RADAR data based on the determined correction factor to calibrate the RADAR data; and determining, with the one or more computing devices, the at least one of the presence of the compaction layer within the field, the location of the compaction layer within the field, or the seedbed depth within the field based on the calibrated RADAR data.

9. The method of claim 8, wherein adjusting the received RADAR data comprises adjusting, with the one or more computing devices, at least one of a time-of-flight, an amplitude, a frequency, or a phase associated with the received RADAR data based on the determined correction factor.

10. The method of claim 8, wherein receiving the first input comprises receiving, with the one or more computing devices, sensor data indicative of the soil moisture content of the field from a soil moisture sensor.

11. The method of claim 10, wherein determining the soil moisture content value comprises updating, with the one or more computing devices, the determined soil moisture content value at a predetermined rate as the agricultural operation is being performed.

12. The method of claim 8, wherein receiving the first input comprises receiving, with the one or more computing devices, at least one of an operator input or an input from a remote server database.

13. The method of claim 8, wherein the at least one of the presence of the compaction layer within the field, the location of the compaction layer within the field, or the seedbed depth within the field corresponds to the at least one of the presence of the compaction layer within the field or the location of the compaction layer within the field.

14. The method of claim 8, wherein the at least one of the presence of the compaction layer within the field, the location of the compaction layer within the field, or the seedbed depth within the field corresponds to the seedbed depth within the field.

\* \* \* \* \*